US009903801B2

(12) United States Patent
Bettacchioli

(10) Patent No.: US 9,903,801 B2
(45) Date of Patent: Feb. 27, 2018

(54) METHOD FOR FOLLOWING DEGASSING RATE BY MEASURING PARTIAL PRESSURES MEASURED BY MASS SPECTROMETRY

(71) Applicant: THALES, Neuilly sur Seine (FR)

(72) Inventor: Alain Roger Dante Bettacchioli, Cannes la Bocca (FR)

(73) Assignee: THALES, Courbevoie (FR)

(*) Notice: Subject to any disclaimer, the term of this patent is extended or adjusted under 35 U.S.C. 154(b) by 577 days.

(21) Appl. No.: 14/473,457

(22) Filed: Aug. 29, 2014

(65) Prior Publication Data
US 2015/0066421 A1    Mar. 5, 2015

(30) Foreign Application Priority Data
Aug. 30, 2013 (FR) ...................................... 13 02014

(51) Int. Cl.
*G01L 7/00* (2006.01)
*G01N 7/14* (2006.01)
(Continued)

(52) U.S. Cl.
CPC ............ *G01N 7/14* (2013.01); *H01J 49/0036* (2013.01); *H01J 49/26* (2013.01)

(58) Field of Classification Search
CPC ... G01N 1/405; G01N 33/0011; G01N 33/203
See application file for complete search history.

(56) References Cited

U.S. PATENT DOCUMENTS 5,413,940 A * 5/1995 Lin ...................... H01L 21/316
257/E21.26
6,149,480 A * 11/2000 Iwasaki .................. H01J 9/027
445/3
(Continued)

FOREIGN PATENT DOCUMENTS

CN       103267705 A    8/2013
WO    2009012919 A1    1/2009

OTHER PUBLICATIONS

N. Schindler, et al., "Measurements of Partial Outgassing Rates", Vacuum, Apr. 1, 1996, pp. 351-355, vol. 47, No. 4, Elsevier Science Ltd, Great Britain, UK, XP055117677.
N. Schindler, et al., "Some Investigations on the Effective Short Time Outgassing Depth of Metals", Journal of Vacuum Science and Technology—Part A, Nov. 1, 1998, pp. 3569-3577, AIP, Melville, NY, USA, XP012004326.
(Continued)

*Primary Examiner* — Elias Desta
(74) *Attorney, Agent, or Firm* — Baker & Hostetler LLP

(57) ABSTRACT

A method for following the degassing of a component placed in a vacuum chamber, comprises: measuring partial pressures $P_i$ for a set M of reference atomic masses, by means of a mass spectrometer connected to the vacuum chamber; determining a degassing rate $\eta$, at least as a function of the measured partial pressures $P_i$; and, calculating a slope of the variation in the degassing rate. The degassing rate $\eta$ may advantageously be determined by calculation by means of a relationship of the type:

$$\eta = \frac{\sum_{i \in M} \alpha_i P_i}{\sum_{i=0}^{N} \alpha_i P_i}$$

where M denotes the set of reference atomic masses, $P_i$ denotes the partial pressures for the atomic masses measured
(Continued)

by the mass spectrometer, the coefficients $\alpha_i$ denote preset weighting coefficients associated with each partial pressure $P_i$, and N denotes a maximum atomic mass for which the partial pressure $P_i$ can be measured by the mass spectrometer.

15 Claims, 3 Drawing Sheets

(51) Int. Cl.
      *H01J 49/00*      (2006.01)
      *H01J 49/26*      (2006.01)

(56) References Cited

U.S. PATENT DOCUMENTS 6,182,376 B1* 2/2001 Shin .................. H01L 21/67109
                                                          34/412
8,268,241 B1    9/2012 Cooper

OTHER PUBLICATIONS

D. Edwards, Jr., "Upper Bound to the Pressure in an Elementary Vacuum System", Journal of Vacuum Science and Technology, Jan. 1, 1977, p. 606, vol. 14, No. 1, XP055117686.
P. Michallon, et al., "Out-Gassing Tool at CEA-LETI", URL:http://www.sematech.org/meetings/archives/litho/euvl/7470/posters.htm, Nov. 7, 2005, XP055117682.

* cited by examiner

METHOD FOR FOLLOWING DEGASSING RATE BY MEASURING PARTIAL PRESSURES MEASURED BY MASS SPECTROMETRY

CROSS-REFERENCE TO RELATED APPLICATION

This application claims priority to foreign French patent application No. FR 1302014, filed on Aug. 30, 2013, the disclosure of which is incorporated by reference in its entirety.

FIELD OF THE INVENTION

The present invention relates to the field of means for testing and preparing components by degassing volatile compounds liberated by a component or system placed in a vacuum chamber, and more particularly it relates to a method for following degassing rate by measuring partial pressures measured by a mass spectrometer connected to the thermal vacuum chamber.

BACKGROUND

In various industries it is necessary, after a component has been manufactured or assembled, to carry out a degassing step under vacuum, this degassing step causing volatile chemical species trapped by this component to desorb. This degassing step is of particular importance in the space field, notably because liberation of chemical species in extra-atmospheric space is associated with a high risk of damage to and contamination of constituents of the spacecraft. Thus, with the aim of ensuring the integrity of equipment such as optical or telecommunication systems for example, it is necessary to degas the components or subsystems of a satellite such as an inertial measurement unit, a solar array drive mechanism, or even the fully assembled satellite platform. Provision is generally made for a number of degassing steps throughout the manufacturing process of the satellite. For example, a composite will be degassed once after its production, a second time after it has been integrated in an operational subsystem, then once more after the final assembly of the satellite.

To carry out these degassing operations various vacuum chambers are used, the capacity of which may vary from one meter cube to as much as typically 500 $m^3$, these chambers also being capable of being heated to temperatures typically comprised between room temperature and 150° C. for vacuum pressures typically comprised between $10^{-5}$ and $10^{-7}$ hPa. Knowing that said degassing operations generally last one to three days, the high industrial cost that such operations represent will be readily apparent.

Depending on the constituent materials of the component or subsystem in question, various volatile chemical compounds are liable to be liberated. For example, in the space field, during the degassing of the insulating product known as multilayer insulation (MLI) or the solar array drive mechanism (SADM), various solvents, water and/or silicon-containing products may be liberated during a thermal vacuum degassing operation.

The degassing processes used at the present time are simple. They generally consist in keeping the component in a vacuum chamber under empirically set vacuum, temperature and time conditions. Thus various protocols have been defined that are applied depending on the component or subsystem in question. By way of example, typically implemented protocols include:

24 hours at 120° C.,
48 hours at 100° C., or
72 hours at 80° C., for a final vacuum level of about $10^{-6}$ hPa.

However, these values are entirely empirical and sometimes based on outdated studies. These degassing operations do not allow the effectiveness of the degassing to be measured during the test. It is therefore possible, under these conditions, for the test to continue several hours after the degassing limit has been reached, or inversely, at the end of the test, for the degassing not to have been completed effectively.

One known technique for measuring the effectiveness of a vacuum degassing operation implements instruments of the quartz balance type. Quartz balances do indeed allow a satisfactory quantitative measurement to be obtained when the mass of the collected deposit remains small in size. These instruments have been employed with success when the equipment to be degassed is an optical system or a system having a low volatile compound content. In contrast, when the equipment to be degassed liberates a large amount of or more contaminating volatile compounds, these instruments reach their limits. In particular, they rapidly saturate and then require regular regenerating operations to degas them. This need for regular regeneration in order to obtain once more a measurement of the deposited mass makes these instruments unsuitable for measuring the effectiveness of the degassing of components employed in the space field. Another difficulty with this technique relates to the precision of the measurement when the temperature of the degassing chamber is very different from the temperature of the boat serving to collect the deposit. In order to make it possible for the volatile compounds to be analysed to condense, the quartz balance then plays the role of a too-effective cold trap; it then rapidly saturates meaning that it must frequently be regenerated. Imprecise measurements result that are unsuitable for effective following of degassing rate during a test.

The challenge is to provide a complete and rapid degassing operation, allowing the length and therefore the cost of the operation to be decreased, and subsequent steps of design or use to be made safe. The techniques currently employed are unsuitable for meeting this need. At the present time it would be desirable to provide a means allowing in real time, during the degassing operation, the degassing rate of a component placed under thermal vacuum to be followed.

SUMMARY OF THE INVENTION

For this purpose, one subject of the invention is a method for following an operation for degassing a component placed in a vacuum chamber, characterized in that it comprises steps consisting in:

periodically measuring partial pressures $P_i$ for a set M of reference atomic masses, by means of a mass spectrometer connected to the vacuum chamber;

periodically determining a degassing rate $\eta$, at least as a function of the partial pressures $P_i$ measured for the set M of reference atomic masses; and periodically calculating and displaying a slope of the variation in the degassing rate $\eta$.

Advantageously, the degassing rate η is determined at least as a function of a weighted sum of the partial pressures $P_i$ measured for the set M of reference atomic masses.

Advantageously, the degassing rate η is determined by calculation by means of a relationship of the type:

$$\eta = \frac{\sum_{i \in M} \alpha_i P_i}{\sum_{i=0}^{N} \alpha_i P_i}$$

in which M denotes the set of reference atomic masses, $P_i$ denotes the partial pressures for the atomic masses measured by the mass spectrometer, the coefficients $\alpha_i$ denote preset weighting coefficients associated with each partial pressure $P_i$, and N denotes a maximum atomic mass for which the partial pressure $P_i$ can be measured by the mass spectrometer.

Advantageously, the set M of reference atomic masses contains at least the following atomic masses: 16, 18, 30, 32 and 44.

Advantageously, the method comprises a prior step of selection from a preset list of the set M of reference atomic masses used to calculate the degassing rate.

Advantageously, the method also comprises a step of selection from a preset list of a set of weighting coefficients $\alpha_i$ associated with the partial pressures $P_i$ of the set M of reference atomic masses in question.

Advantageously, the weighting coefficients $\alpha_i$ employed in the calculation of the degassing rate are all equal to 1.

Advantageously, the method comprises a step consisting in periodically determining a stopping criterion of the degassing operation, at least as a function of the slope of the variation in the degassing rate η. The stopping criterion may be determined at least by comparing the slope of the variation in the degassing rate η with a preset value. It may also be determined at least by comparing, with a preset value, the ratio of the periodically determined slope of the variation in the degassing rate η to an initially determined slope of the variation in the degassing rate $\eta_o$. Lastly, it may be determined as a function of the slope of the variation in the degassing rate η and the ratio of the periodically determined slope of the variation in the degassing rate η to an initially determined slope of the variation in the degassing rate $\eta_o$.

Advantageously, the method comprises a step consisting in modifying temperature and pressure conditions in the vacuum chamber as a function of the degassing rate η or the slope of the variation in the degassing rate.

Advantageously, the method comprises a step of alerting an operator of the vacuum chamber as a function of the degassing rate η or the slope of the variation in the degassing rate.

The invention also relates to a mass spectrometer comprising a control module configured to implement the method having the features described above.

The invention finally relates to a degassing device comprising a vacuum chamber intended for degassing a component, and a mass spectrometer having the features described above.

BRIEF DESCRIPTION OF THE DRAWINGS

The invention will be better understood and other advantages will become apparent on reading the detailed description of embodiments given by way of example in the following figures.

For the sake of clarity, the same elements have been given the same references in the various figures.

DETAILED DESCRIPTION

Figure 1:
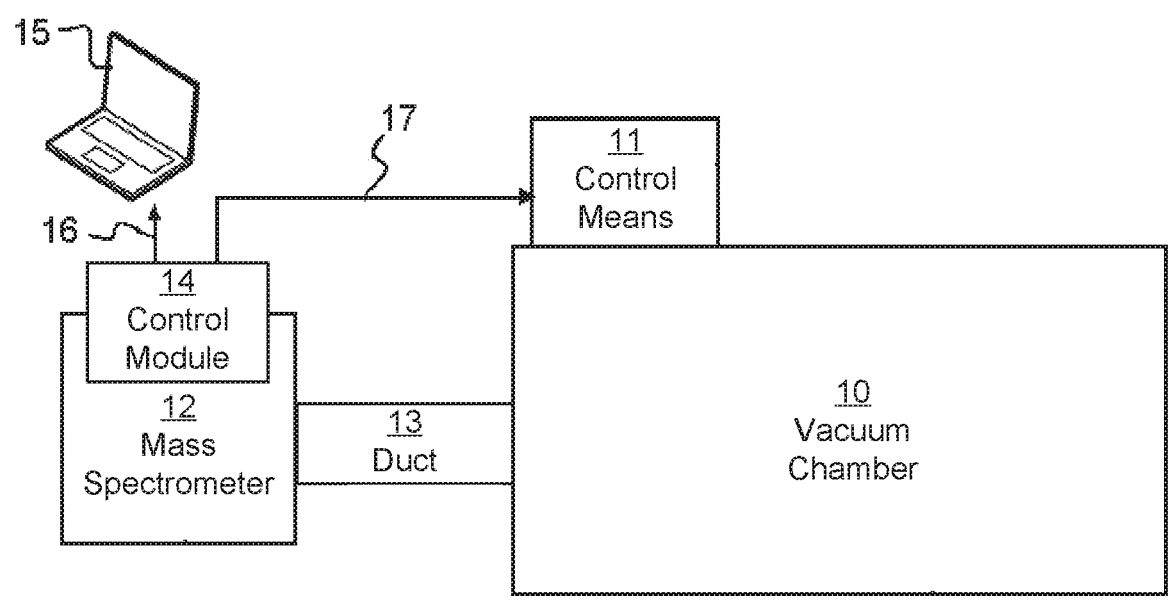
FIG. 1 shows a degassing device for implementing the method according to the invention.

FIG. 1 shows a degassing device for implementing the method according to the invention. The device comprises a vacuum chamber 10 into which a component to be degassed may be placed. The device also comprises means 11 able to control the pressure and temperature of the vacuum chamber. The vacuum chamber is pumped out and kept under vacuum for a length of time that varies depending on the amount of water held by the materials, the pressure remaining close to $10^{-3}$ hPa. When the partial vapour pressure drops below a certain threshold the pressure decreases and at the end of the test, i.e. at the end of the time allowed, the pressure generally neighbours $10^{-6}$ hPa as mentioned above. The temperature of the chamber may also be controlled in order to accelerate the desorption effect.

The device also comprises a mass spectrometer 12 connected to the vacuum chamber 10 by way of a duct 13. A current mass spectrometer 12 is used, typically comprising a source in which a fraction of the molecules present is ionized, a dispersing system capable of separating the various atomic masses output from the source, and an analyser capable of measuring the relative abundance of the atomic masses. Thus, the analyser determines a partial pressure $P_i$ for each of the atomic masses on a scale most often ranging from 0 to 100, or 200, or even 300 depending on the configuration of the spectrometer.

The device also comprises a control module 14 allowing the method for following degassing rate to be implemented. According to the invention, the method for following degassing rate described below comprises calculating steps that may be implemented by means of various media. They may for example be implemented in the control software of the mass spectrometer, or even in a separate electronic module 14 connected to the mass spectrometer 12, as shown in FIG. 1. As will be described below, the method determines a degassing rate and a stopping criterion of the degassing, these items of information may then be displayed so that an operator can see them, for example by means of a computer screen 15. For this purpose, the module 14 may be connected to a computer screen 15 by a connection 16. It is also envisaged to use these items of information to control the vacuum chamber, typically to control its return to room temperature when the method determines that the stopping criterion is met. As shown in FIG. 1, the module 14 may be connected to the control means 11 of the vacuum chamber 10 by way of a connection 17.

Figure 2:
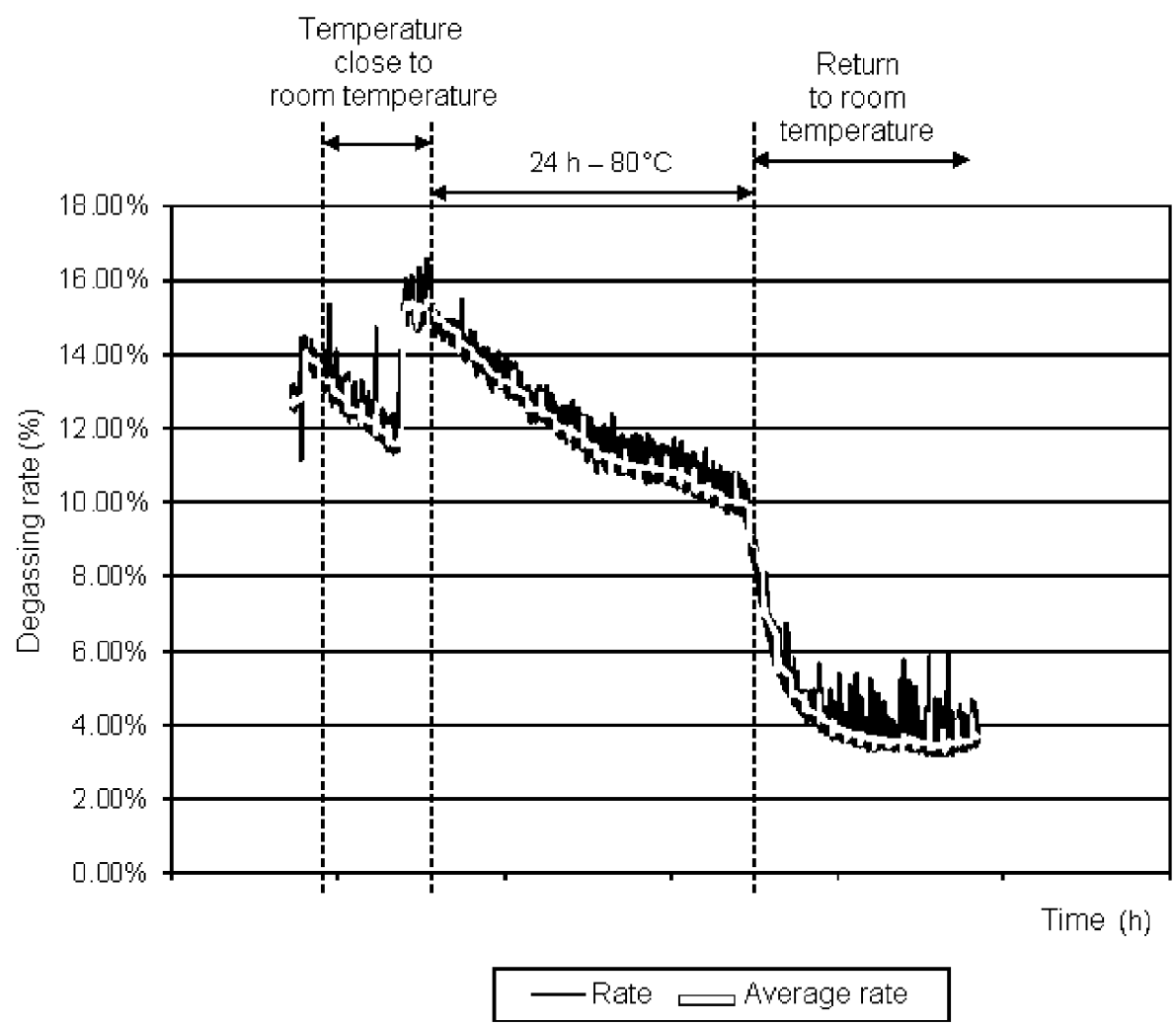
FIG. 2 shows a graph of the variation in the degassing rate obtained with the method according to the invention.

FIG. 2 shows a graph of the time variation of the degassing rate, which variation is obtained by the method according to the invention. When a component to be degassed is placed in the vacuum chamber 10, the latter may liberate various chemical species as described above. The mass spectrometer 12 connected to the vacuum chamber allows partial pressures $P_i$ to be determined for the atomic masses resulting from the ionization of these species. This measurement may be carried out periodically at a preset time interval that is optionally adjustable by an operator. The method according to the invention first comprises a step consisting in selecting a set M of reference atomic masses. This set of reference atomic masses is a subset of the atomic masses measurable by the mass spectrometer, typically comprised between 1 and 100 when the maximum atomic mass of the spectrometer is 100. This set of reference atomic masses is selected depending on the chemical species liberated by the component. For example, for a component that is known to be liable to liberate water, silicon-containing products and benzene, the set M of reference atomic masses adopted is:

M={16, 18, 30, 32, 44, 58, 62, 72, 78, 86, 92};

with the aim of following the degassing of silane ($SiH_4$, atomic mass of 32), disilane ($Si_2H_6$, atomic mass of 62), trisilane ($Si_3H_8$, atomic mass of 92) and benzene (atomic mass of 78) species. Specifically, it has been observed that in the presence of desorption of high molecular masses, chemical compounds of lower molecular masses, typically comprised between 1 and 100, are also liberated. Thus, in this example, following the silicon-based compounds also has the aim of revealing the desorption of silicon-containing compounds of higher molecular masses.

The method comprises a step consisting in periodically determining, generally using the same time interval as that used in the mass spectrometry measurements, a degassing rate $\eta$, at least as a function of a weighted sum of the partial pressures $P_i$ measured for the set M of reference atomic masses.

In a preferred embodiment of the invention, this degassing rate $\eta$ is determined by calculation by means of a relationship of the type:

$$\eta = \frac{\sum_{i \in M} \alpha_i P_i}{\sum_{i=0}^{N} \alpha_i P_i}$$

in which M denotes the set of reference atomic masses, the variables $P_i$ denote the partial pressures for the reference atomic masses measured by the mass spectrometer, the coefficients $\alpha_i$ denote weighting coefficients associated with each partial pressure $P_i$, and N denotes the largest atomic mass measured by the mass spectrometer (typically $100 \leq N \leq 300$ depending on the range of the spectrometer used).

Other calculational formulae are also possible without departing from the scope of the present invention. It is for example possible to determine a degassing rate by only summing the partial pressures $P_i$, the weighting coefficients $\alpha_i$ then being set equal to 1.

However, it has been demonstrated that the above formula makes particularly effective following of the degassing rate possible, in particular when N=100. This is because gaseous compounds such as nitrogen or oxygen contribute to a greater extent to the overall pressure in the spectrometer. The sum which figures in the denominator in the above formula is quite close to this overall pressure in the spectrometer but it is slightly different therefrom due to the limited number N of molar masses identified. Calculating the degassing rate $\eta$ by taking the ratio of the sum of the optionally weighted partial pressures of the species of interest (water, silicon-containing products, benzene, etc.) to the sum of the optionally weighted partial pressures of all of the measured atomic masses makes effective qualitative following possible during the degassing.

FIG. 2 shows the time variation of this degassing rate during a degassing test comprising a first phase carried out at a temperature near room temperature, followed by a second phase carried out at a temperature of 80° C. for a time of 24 hours, followed by a third phase in which room temperature is returned to. This figure shows, first in the first phase, the variation of the degassing criterion under the effect of application of a vacuum without use of heaters. In the second phase, which makes up the veritable degassing thermal vacuum test, stimulation of the degassing by temperature is perfectly clear from the jump in the graph, i.e. the jump in the rate of desorption from the materials. This desorption rate gradually decreases during the test. The method according to the invention therefore does not attempt to quantitatively determine a desorbed mass but, in contrast to known techniques, it advantageously allows the variation in the degassing during the test to be determined. It is possible to visualize a trend in the variation of the degassing rate in real time. This trend in the variation is an essential feature as it will allow the length of the degassing operation to be better defined by allowing, for example, a stopping criterion to be defined for this operation, as described by means of the following figure.

Figure 3:
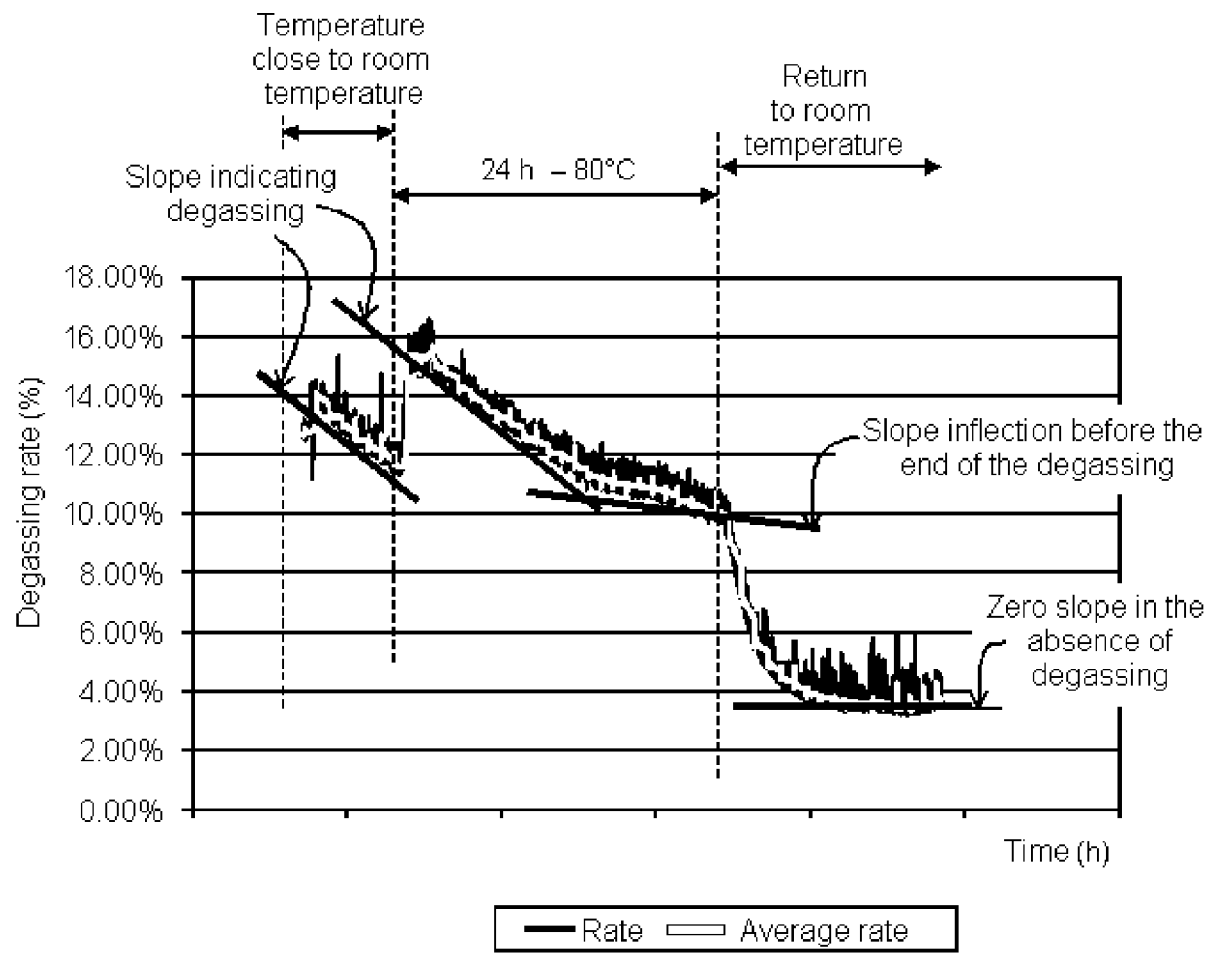
FIG. 3 illustrates the principle used to determine the slope of the variation in the degassing rate by the method according to the invention.

FIG. 3 illustrates the principle of the method used to determine the slope of the variation in the degassing rate according to the invention. Following the step of calculating the degassing rate $\eta$ such as described above, the method may comprise a filtering step. Various techniques for filtering the degassing rates calculated for each time interval may be envisaged, a moving average as shown by the thick black line in FIGS. 2 and 3 or a median filter or a Kalman filter notably coming to mind. The method then comprises a step consisting in periodically calculating and displaying, generally using the same time interval as that used in the degassing rate calculation, a slope of the variation in the degassing rate $\eta$. Typically, this slope is defined as the difference between two degassing rates determined in succession, divided by the time interval between two calculations. This slope of the variation is schematically shown by means of thick black lines in FIG. 3. In the first phase of the test, carried out at a temperature close to room temperature, the degassing rate is observed to have a substantially constant slope. In the second phase of the test, carried out at a temperature of 80° C. for a time of 24 hours, it may be observed that the slope slowly varies and tends to a slope of zero. In the third phase of the test, the slope is substantially zero from the moment that the temperature is returned to room temperature.

The degassing rate does not tend exactly to zero because, apart from a few traces of volatile products that continue to be liberated by the materials under test in negligible proportions, there is no longer a pumping dynamic in the vacuum chamber and the pressure remains constant as do the densities of the various products that compose the atmosphere thereof: the pumping group having then reached its performance limits, there may be considered to be almost no particulate exchange between the interior and exterior of the enclosure, excepting leaks.

The method according to the invention allows the degassing operation to be followed in real time, by means of calculation and operator-viewable display of the slope of the variation in the calculated degassing rate. When the operator observes that the slope is no longer varying or that it has dropped below a given criterion, it may then be decided to stop the degassing operation. Following the slope during the return to room temperature allows, a posteriori, the effectiveness of the degassing operation to be followed.

In order to automate and make the stopping of the degassing operation more reliable, it is also envisaged in the method according to the invention to determine a stopping criterion, at least as a function of the slope of the variation in the degassing rate η. For example, the stopping criterion may be determined by comparing the slope of the variation in the degassing rate η with a preset value. The stopping criterion may also be determined by comparing, with a preset value, the ratio of the periodically determined slope of the variation in the degassing rate η to an initially determined slope of the variation in the degassing rate $η_o$. Alternatively, stopping of the degassing operation may even be determined as a function of both these criteria.

In a first embodiment, the stopping criterion may be displayed on an operator-viewable screen with the aim of notifying the operator of the end of the degassing operation. In other words, the method may advantageously comprise an alerting step, intended for an operator of the vacuum chamber, depending on the stopping criterion.

In another embodiment, the stopping criterion may also be used to control the vacuum chamber 10. Typically, when the stopping criterion indicates the end of the degassing operation, for example when the slope of the variation in the degassing rate is lower than a preset value, the vacuum chamber is returned to room temperature. In other words, the method according to the invention may comprise a step consisting in modifying temperature and pressure conditions in the vacuum chamber as a function of the stopping criterion.

Of course, the above two embodiments are merely non-limiting examples of automation of the degassing operation, made possible by the method for following degassing rate according to the invention. More generally, the invention relates to the method for calculating degassing rate determined by means of partial pressures of a set of reference atomic masses selected depending on the component to be degassed; and to the use of this degassing rate to control the degassing operation, in particular by controlling the conditions in the vacuum chamber containing the component to be degassed.

It is also envisaged in the present invention to define a list of sets of reference atomic masses; each set of reference atomic masses being particularly suitable for following the degassing of a certain type of component. As was indicated above, it has been demonstrated that a set $M_1$ made up of the atomic masses 16, 18, 30, 32, 44, 58, 62, 72, 78, 86 and 92 is particularly suitable for following the degassing of components liable to liberate silicon-containing products. It is envisaged based on the same principle to define other sets $M_2$, $M_3$, etc. that are respectively suitable for following the degassing of components liable to liberate other chemical species. Thus, the method according to the invention may comprise a prior step of selecting from a preset list (then containing the sets $M_1$, $M_2$, $M_3$, etc.) the set of reference atomic masses used to calculate the degassing rate.

Based on the same principle, it is also envisaged to associate with each set of reference atomic masses a number of sets of weighting coefficients $α_i$ associated with the partial pressures Pi of the set M of reference atomic masses in question. Thus, after having selected a set of reference atomic masses, from the list comprising the sets $M_1$, $M_2$, $M_3$, etc., the operator may then select a set of weighting coefficients from a preset list; the advantage of such an option notably being to allow a number of formulae for calculating the degassing rate to be tested and displayed in order to select, in real time or a posteriori, the formula allowing the most precise following of the degassing rate.

The invention also relates to a mass spectrometer comprising a control module 14 configured to implement the method having the features described above.

Lastly, the invention relates to a degassing device comprising a vacuum chamber 10 intended for degassing a component, and a mass spectrometer 12 configured to implement the method described above.

The invention claimed is:

1. A method of degassing a component, the method comprising:
    placing the component in a vacuum chamber;
    reducing a pressure in the vacuum chamber by pumping air out of the vacuum chamber;
    periodically measuring, with a mass spectrometer, partial pressures $P_i$ for a set M of reference atomic masses, the mass spectrometer being connected to the vacuum chamber;
    periodically determining a degassing rate η, at least as a function of the partial pressures $P_i$ measured for the set M of reference atomic masses, by calculating:

$$\eta = \frac{\sum_{i \in M} \alpha_i P_i}{\sum_{i=0}^{N} \alpha_i P_i}$$

wherein M denotes the set of reference atomic masses, $P_i$ denotes the partial pressures for the atomic masses measured by the mass spectrometer, coefficients $α_i$ denote preset weighting coefficients associated with each partial pressure $P_i$, and N denotes a maximum atomic mass for which the partial pressure $P_i$ can be measured by the mass spectrometer; and
    controlling the degassing as a function of at least one of said degassing rate η and a variation in the degassing rate η.

2. The method according to claim 1, wherein the set M includes at least the following atomic masses: 16, 18, 30, 32 and 44.

3. The method according to claim 1, further comprising selecting the set M from a preset list of reference atomic masses prior to calculating the degassing rate.

4. The method according to claim 1, further comprising selecting the weighting coefficients $α_i$ from a preset list of weighting coefficients.

5. The method according to claim 1, wherein the weighting coefficients $α_i$ are all equal to 1.

6. The method according to claim 1, further comprising periodically determining a stopping criterion as a function of at least a slope of the variation in the degassing rate η.

7. The method according to claim 6, wherein the stopping criterion is determined at least by comparing the slope of the variation in the degassing rate η with a preset value.

8. The method according to claim 6, wherein the stopping criterion is determined at least by comparing a ratio of the determined slope of the variation in the degassing rate to a predetermined slope of the variation in the degassing rate $η_o$.

9. The method according to claim 6, wherein the stopping criterion is determined as a function of the slope of the variation in the degassing rate η and a ratio of the determined slope of the variation in the degassing rate to an initially determined slope of the variation in the degassing rate $η_o$.

10. The method according to claim 1, further comprising generating an alert to an operator based on the degassing rate η or the slope of the variation in the degassing rate.

11. A mass spectrometer comprising a control module configured to implement the method according to claim 1.

12. A degassing device comprising:
a vacuum chamber configured to degas a component; and
a mass spectrometer according to claim 11.

13. The method according to claim 1, wherein controlling the degassing comprises modifying a temperature and the pressure in the vacuum chamber.

14. The method according to claim 1, further comprising periodically calculating and displaying, on a screen, a slope of the variation in the degassing rate η.

15. The method according to claim 1, further comprising:
periodically calculating a slope of the variation in the degassing rate η;
periodically determining a stopping criterion as a function of said slope of the variation in the degassing rate η; and
alerting an operator based on the stopping criterion.

* * * * *